United States Patent [19]

Nagata et al.

[11] Patent Number: 5,723,672

[45] Date of Patent: Mar. 3, 1998

[54] PROCESS FOR RACEMIZATION OF OPTICALLY ACTIVE 1-PHENYLETHYLAMINE DERIVATIVE

[75] Inventors: Shinichiro Nagata, Oita; Yoshimi Yamada, Osaka; Koji Hagiya, Takatsuki; Hideyuki Goto, Oita, all of Japan

[73] Assignee: Sumitomo Chemical Company, Limited, Osaka, Japan

[21] Appl. No.: 759,633

[22] Filed: Dec. 5, 1996

[30] Foreign Application Priority Data

Dec. 7, 1995 [JP] Japan ................................ 7-318851

[51] Int. Cl.⁶ ........................................... C07C 209/00
[52] U.S. Cl. ................................. 564/424; 564/271
[58] Field of Search ................................ 564/424, 271

[56] References Cited

U.S. PATENT DOCUMENTS

| 4,252,744 | 2/1981 | Bison et al. . | |
|---|---|---|---|
| 5,504,253 | 4/1996 | Van Wagenen et al. | 564/374 |

FOREIGN PATENT DOCUMENTS

| 0489682 | 11/1991 | European Pat. Off. . |
| 2851039 | 11/1978 | Germany . |
| 7-188120 | 7/1995 | Japan . |
| 4275258 | 9/1996 | Japan . |
| 1471389 | 8/1974 | United Kingdom . |

OTHER PUBLICATIONS

*Patent Abstracts of Japan*, Publication No. 08027073 (EPO) (1996).

*Patent Abstracts of Japan*, Publication No. 07188120 (EPO) (1993).

Hashimoto et al. (1995) *Tetrahedron letters*, vol. 36, No. 48, pp. 8821–8824.

*Primary Examiner*—Brian M. Burn
*Attorney, Agent, or Firm*—Birch, Stewart, Kolasch & Birch, LLP

[57] ABSTRACT

A process for racemization of an optically active 1-phenylethylamine derivative represented by formula (I):

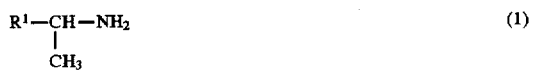

wherein $R^1$ represents a phenyl group substituted at least at the ortho-position, which comprises reacting the optically active 1-phenylethylamine derivative (1) with an aldehyde compound represented by formula (2):

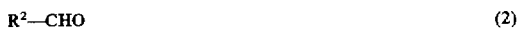

where $R^2$ represents an optionally substituted alkyl group or an optionally substituted phenyl group to form an optically active imine represented by formula (3):

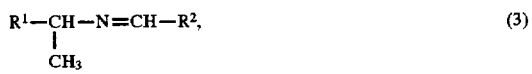

reacting the imine with an alkaline metal tert-alkoxide in an aprotic solvent, and then hydrolyzing the resultant racemic imine.

5 Claims, No Drawings

PROCESS FOR RACEMIZATION OF OPTICALLY ACTIVE 1-PHENYLETHYLAMINE DERIVATIVE

BACKGROUND OF THE INVENTION

1. Field of the Invention

The present invention relates to a process for racemization of certain optically active 1-phenylethylamines.

2. Description of the Related Art

Optically active 1-phenylethylamines are useful compounds as production intermediates of pesticides such as fungicides (a certain racemate is described in Japanese Patent Kokai (Laid-Open) No. 2-76846, and a certain optically active substance is described in Japanese Patent Kokai (Laid-Open) No. 2-11550), reagents for optical resolution and the like. As an example of the production process thereof, the process of producing certain optically active 1-phenylethylamines due to optical resolution of a racemate is described in Japanese Patent Kokai (Laid-Open) No. 2-306942. In such a process of producing an optically active substance due to optical resolution, however, effective utilization of an undesirable antipode remained after isolating one useful optically active substance. Therefore, reutilization of the antipode due to racemization becomes an important industrial object.

As for the process for the racemization of optically active 1-(4-chlorophenyl)ethylamine, a process of reacting the amine with potassium tert-butoxide in dimethyl sulfoxide has hitherto been described in Japanese Patent Kokai (Laid-Open) No. 4-275258. It was found by the intensive study of the present inventors that, according to the process, the racemization reaction of optically active 1-(2,4-dichlorophenyl)ethylamine does not proceed at all and the process can not be applied to the racemization of optically active 1-phenylethylamines having a substituent at the ortho-position.

On the other hand, the process of converting optically active 1-phenylethylamines into a corresponding imine and then racemizing the imine, the process of dehydration-condensing optically active 1-(4-chlorophenyl)ethylamine with acetophenone, followed by reacting with potassium tert-butoxide has hitherto been described in Japanese Patent Kokai (Laid-Open) No. 7-188120. This process has a problem in that a large amount of an undesirable amine is formed as a by-product after hydrolysis because isomerization (migration of double bond) of the imine proceeds simulataneously as the racemization reaction.

SUMMARY OF THE INVENTION

Under these circumstances, the present inventors have intensively studied a useful process for the racemization of an optically active 1-phenylethylamine derivative having substituent(s) at the ortho-position, which is represented by the following formula [1]. As a result, it has been found that the optically active 1-phenylethylamine derivative represented by the following formula [1], can be efficiently racemized by reacting the optically active 1-phenylethylamine derivative represented by the following formula [1], with an aldehyde compound represented by the following formula [2], to form an optically active imine represented by the following formula [3], reacting the imine with an alkaline metal tert-alkoxide in an aprotic polar solvent or a mixture of the aprotic polar solvent and an aprotic nonpolar solvent, followed by hydrolyzing. Thus, the present invention has been accomplished.

That is, the present invention provides a process for the racemization of an optically active 1-phenylethylamine derivative represented by the formula [1]:

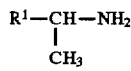  [1]

wherein $R^1$ represents a phenyl group substituted at least at the ortho-position, which comprises reacting the optically active 1-phenylethylamine derivative [1] with an aldehyde compound represented by the formula [2]:

$R^2$—CHO  [2]

wherein $R^2$ represents an optionally substituted alkyl group or an optionally substituted phenyl group to form an optically active imine represented by the formula [3]:

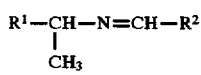  [3]

wherein $R^1$ and $R^2$ are as defined above (hereinafter referred to as a "reaction 1"), reacting the imine with an alkaline metal tert-alkoxide in an aprotic polar solvent or a mixture of the aprotic polar solvent and an aprotic nonpolar solvent (hereinafter referred to as a "reaction 2"), and then hydrolyzing the resultant racemic imine (hereinafter referred to as a "reaction 3").

In the above formulas [1] and [3], one preferred embodiment of $R^1$ is a group represented by the formula [4]:

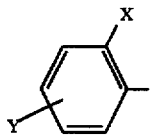  [4]

wherein X represents a halogen atom (for example, a chlorine atom, etc.) or a lower alkyl group (for example, $C_1$–$C_4$ alkyl group such as a methyl group,), and Y represents a halogen atom (for example, chlorine atom,), a lower alkyl group, for example, a $C_1$–$C_4$ alkyl group such as methyl group,) or a hydrogen atom. A more preferred embodiment of $R_1$ is a 2,4-dichlorophenyl group. In the above formulas [2] and [3], one preferred embodiment of $R^2$ is a lower alkyl group (for example, a $C_1$–$C_4$ alkyl such as tert-butyl group, isopropyl, isobutyl, etc.).

The present invention also provides an optically active or racemic imine compound represented by the formula [5]:

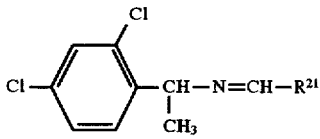  [5]

wherein $R^{21}$ represents a lower alkyl group (for example, a $C_1$–$C_6$ alkyl group such as tert-butyl, isopropyl, isobutyl, etc.

According to the process of the present invention, formation of a compound represented by the formula [6]:

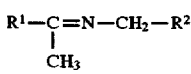  [6]

wherein $R^1$ and $R^2$ are as defined above, which has an isomerized product wherein a double bond of the optically active imine of the above formula [3] is migrated, can be inhibited and, therefore, formation of an amine as they by-product represented by the formula [7]:

$R^2$—$CH_2$—$NH_2$  [7]

wherein $R^2$ is as defined above which is obtained by hydrolyzing the isomerized product [6] can be inhibited.

DESCRIPTION OF THE PREFERRED EMBODIMENT

The present invention will be explained in detail, hereinafter.

First, the reaction 1 will be explained in detail.

the optically active 1-phenylethylamine derivative represented by the formula [1], used as the starting material may be R-form or S-form, or a mixture containing an excess of ether one of them. The substituent which is substituted at least at the ortho position on the phenyl group (the phenyl group being represented by $R^1$ of the formula [1]), may be any substituent which does not inhibit the reaction, and is not specifically limited.

The substituent in the optionally substituted alkyl group or optionally substituted phenyl group which is represented by $R^2$ of the formula [2], used as another starting material may be any substituent which does not inhibit the reaction, and is not specifically limited. Examples of $R^2$ include a $C_1$-$C_6$ alkyl group, such as an isobutyl group, a neopentyl group, a isopropyl group, a sec-butyl group, a sec-pentyl group, an isopentyl group, and a tert-butyl group, etc., a phenyl group, a 4-methylphenyl group, a 4-chlorophenyl group, a 2,4-dichlorophenyl group and the like. Specific examples of the aldehyde compound represented by the formula [2], include isovaleraldehyde, 3,3-dimethylbutylaldehyde, isobutylaldehyde, 2-methylbutylaldehyde, 2-ethylbutylaldehyde, 2-methylvaleraldehyde, pivalaldehyde, benzaldehyde, 4-methylbenzaldehyde, 4-chlorobenzaldehyde, 2,4-dichlorobenzaldehyde and the like. The amount of the aldehyde compound [2] used is normally from 0.5 to 5 mol, and preferably from 0.95 to 2 mol, based on 1 mol of the optically active 1-phenylethylamine derivative represented by the formula, [1].

The reaction is normally conducted in a solvent in the presence of a catalyst, but can also be conducted without using the solvent. When using the solvent, the solvent used may be any one which does not inhibit the reaction. Examples thereof include aromatic hydrocarbon solvents such as toluene, benzene, xylene, etc. ether solvents such as dioxane, methyl-tert-butyl, etc; aliphatic hydrocarbon solvents such as hexane, heptane, etc.; and halogenated hydrocarbon solvents such as dichloroethane, chloroform, chlorobenzene, etc. The amount of the solvent used is normally from 1 to 20 parts by weight, preferably from 3 to 10 parts by weight, based on 1 part by weight of the optically active 1-phenylethylamine derivative represented by the formula [1]. Examples of the reaction catalyst which is optionally used include sulfonic acids such as benzenesulfonic acid, p-toluenesulfonic acid and the like. The amount of the catalyst is normally from 0.001 to 0.1 mol, and preferably from 0.005 to 0.05 mol, based on 1 mol of the optically active 1-phenylethylamine derivative represented by the formula [1].

The reaction temperature is normally within a range from about 70° to 180° C. and the reaction time is normally within a range from 0.5 to 24 hours. It is preferred to react while the formed water is removed out of the system by using a water isolator.

The formed optically active imine represented by the general formula [3], may be used for the reaction 2 as it is after the reaction solution was cooled and optionally washed with water to remove the catalyst, or the imine may be used for the reaction 2 after it was isolated by low-boiling fractional distillation. The image may also be used for the reaction 2 after it was optionally purified by means such as distillation, recrystallization, or various chromatographies.

Next, the reaction 2 will be explained in detail.

Examples of the alkaline metal tert-alkoxide used include alkaline metal tert-$C_4$-$C_5$ alkoxides such as potassium tert-butoxide, sodium tert-butoxide, potassium tert-pentyloxide, sodium tert-pentyloxide and the like. The amount of the alkaline metal tert-alkoxide used is normally from 0.01 to 2 mol, preferably from 0.05 to 0.3 mol, based on 1 mol of the optically active imine of the general formula [3]. It is advantageous to use potassium tert-butoxide or sodium tert-butoxide as the alkaline metal tert-alkoxide in view of industrial availability.

As the aprotic polar solvent used, those having a dielectric constant of not less than 22 are preferred, and examples thereof includes N,N-dimethylformamide, dimethyl sulfoxide, N,N-dimethylacetamide, N-methylpyrrolidone, 1,3-dimethyl-2-imidazolidinone, sulfolane, nitromethane, acetonitrile, N,N'-dimethylpropyleneurea and the like. Preferred examples thereof include N,N-dimethylformamide and dimethyl sulfoxide. When using only the aproptic polar solvent as the solvent, the amount of it is normally from 0.5 to 20 parts by weight, based on 1 part by weight of the optically active imine of the general formula [3]. When using a mixture of the aproptic polar solvent and aproptic nonpolar solvent as the solvent, examples of the aprotic nonpolar solvent include aromatic hydrocarbon solvents such as benzene, toluene, xylene and the like; halogenated hydrocarbon solvents such as chlorobenzene and the like; ether solvents such as diethyl ether, methyl-tert-butyl ether and the like; and aliphatic hydrocarbon solvents such as hexane, heptane and the like. The amount of the solvent used varies depending on the kind of the solvent used, but is normally from 0.5 to 100 parts by weight, and preferably from 1 to 10 parts by weight, based on 1 part by weight of the optically active imine of the formula [3]. The amount of the aproptic polar solvent used is normally from 0.5 to 2 parts by weight, based on 1 part by weight of the optically active imine of the formula [3]. From a practical standpoint, it is advantageous to use a mixture of the aprotic polar solvent and the aproptic nonpolar solvent as the solvent and to use an aromatic hydrocarbon solvent as the aprotic nonpolar solvent.

The reaction temperature and reaction time vary depending on the kind or amount of the alkaline metal tert-alkoxide and kind or amount of the solvent. The reaction temperature is normally within a range from 0° C. to the boiling point of the solvent or 150° C., preferably from 20° to 100° C. The reaction time is normally within a range from 0.5 to 48 hours.

The reaction can be followed by a process of collecting an aliquot of the reaction mixture and measuring a rotation angle, or subject it to a high performance liquid chromatography with an optically active column after hydrolysis.

The formed racemic imine of the formula [2], can be used for the reaction 3, for example, after the aprotic polar solvent and the like is removed from the reaction mixture by washing with water or an aqueous solution containing an inorganic salt such as sodium chloride. For examle, the racemic imine may be used for reaction 3 after it is isolated by low-boiling fraction distillation or the like, or it may be used for reaction 3 after it is optionally purified by means such as distillation, recrystallization, various chromatographies and the like.

Next, the reaction 3 will be explained in detail. The reaction 3 can be conducted under normal hydrolysis reaction conditions, and one embodiment thereof is as follows.

The reaction is conducted, for example, in the presence or acids such as dilute hydrochloride acid, sulfuric acid and the like. In this case, acids are normally used in an amount within a range from 1 to 100 mol, preferably from 1.05 to 20 mol. based on 1 mol of the racemic imine of the formula [3]. Water is normally used in an amount within a range from 1 to 1000 mol, preferably from 20 to 200 mol, based on 1 mol of the racemic imine of the formula [3].

In the reaction, an organic solvent may be used. When using the organic solvent, the organic solvent may be any one which does not inhibit the reaction. Examples thereof include alcohol solvents such as methanol, ethanol and the like; aliphatic hydrocarbon solvents such as hexane, heptane and the like; halogenated hydrocarbon solvents such as dichloroethane, chloroform and the like; ester solvents such as ethyl acetate and the like; ether solvents such as diethyl ether, methyl-tert-butyl ether and the like; and aromatic hydrocarbon solvents such as toluene, xylene, chlorobenzene and the like. The amount of the organic solvent used is normally from 0.1 to 5 parts by weight, based on 1 part by weight of the racemic imine of the formula [3].

The reaction temperature and reaction time vary depending on the kind or amount of acids. The reaction temperature is normally within a range from 0° C. to the boiling point of the solvent or 100° C., preferably from 50° to 90° C. The reaction time is normally within a range from about 10 minutes to 5 hours.

When reaction 3 is conducted, for example, in the presence of acids, a water-soluble salt of a racemate of the 1-phenylethylamine derivative of the formula [1] and acids, and the aldehyde compound of the formula [2] are formed. When using no organic solvent, the desired racemate of the 1-phenylethylamine derivative of the formula [1], can be isolated by adding a water-insoluble solvent to the reaction solution after the completion of the reaction to extract and isolate the aldehyde compound of the formula [2], and other impurities in the organic layer, alkalifying the aqueous layer with an aqueous alkaline solution such as aqueous sodium hydroxide solution and the like, extracting this with a water-insoluble solvent and then concentrating the resultant organic layer under reduced pressure. When using a water-soluble solvent such an alcohol solvent and the like, the treatment is conducted according to the same manner as that described above, after distilling off the water-soluble solvent. When using a water insoluble solvent, the treatment may be conducted according to the same manner as that described above except that the reaction mixture is partitioned as it is to extract the aldehyde compound of the formula [2] in the organic layer. The desired derivative can also be isolated by steam-distilling the reaction mixture to isolate the aldehyde compound of the formula [2] and other non-basic organic impurities, alkalifying the resultant layer, with an aqueous alkaline solution such as aqueous sodium hydroxide solution and the like, extracting this with a water-insoluble solvent and then concentrating the resultant organic layer under reduced pressure.

In the above post-treatment, the aldehyde compound of the formula [2] extracted in the organic layer or aldehyde compound distilled and removed from the reaction solution can be optionally isolated from impurities using an operation such as distillation and the like and reused in the reaction 1.

EXAMPLE

The following Examples further illustrate the present invention in detail but are not to be construed to limit the scope thereof. In the Examples, "% s'" are by weight unless otherwise stated.

The conditions of gas chromatography in the following Examples are as follows.

Apparatus: Shimadzu GC-14A
Column: DB-17 30 m, megabore: 0.53 mm, film thickness: 1 μm
Injection temperature: 250° C.
Column temperature: raised from 100° C. (0 minute) to 250° C. (5 minute) in a rate of 5° C./minute
Carrier gas and flow rate thereof: He, 5 ml/minute
Detection: FID In the following Examples, all optical isomer ratios were determined by high performance liquid chromatography using an optically active column and conditions thereof are as follows.

Apparatus: Shimadzu SPD-6A (UV detector)
LC-6A
column: SUMICHIRAL OA-4100, 5 μm, 4.6 mm in diameter×25 cm in length
Mobile phase: Hexane:ethanol:$CF_3CO_2H$=240:10:1 (v/v/v) 1 mol/minute
Detection: UV 254 nm Example 1

(1) To a mixture of optically active 1-(2,4-dichlorophenyl) ethylamine (optical isomer ratio: S-form/R-form=62.5/37.5) (60 g), pivalaldehyde (2,2-dimethylpropanol) (54.2 g) and toluene (600 g) was added p-toluenesulfonic acid (0.6 g), and then the mixture was heated under reflux while the formed water was removed from the system by using a water isolator for 5 hour.

The reaction solution was cooled to 20° C. and washed with water (300 g). Toluene was distilled off from the organic layer after partitioning to obtain 79.0 g of optically active N-neopentylidene-α-(2,4-dichlorophenyl)ethylamine as a pale yellow oil. The yield thereof after the correction of purity due to gas chromatography was 92.5%.

$^1$H-NMR (CDCl$_3$/TMS) δvalue (ppm): 1.1 (s, 9H), 1.4 (d. 3H), 4.7 (q, 1H), 7.2–7.7 (m, 4H).

(2) To this optically active N-neopentylidene-α-(2,4-dichlorophenyl)ethylamine (10 g) were added toluene (100 g) and N,N-dimethylformamide (10 g) and then sodium tert-butoxide (0.74 g), and the mixture was stirred at 75° C. for 9 hours. At this time, an aliquot of the reaction mixture was collected and the isomerization rate of N-neopentylidene-α-(2,4-dichlorophenyl)ethylamine was measured by gas chromatography. The ratio of N-(α-methyl-2,4-dichlorobenzyldiene)-neopentylamine as the isomerized product was as follows: N-neopentylidene-α-(2,4-dichlorophenyl)ethylamine:N-(α-methyl-2,4-dichlorobenzylidene)-neopentylamine=93.4:6.6. This reaction mixture was cooled to 25° C. and poured into water (100 g), followed by stirring at 25° C. for 5 minutes. After the mixture was allowed to stand and partitioned, the aqueous layer was extracted with toluene (50 g) and then mixed with the organic layer obtained by the partition above.

(3) To this organic layer was added aqueous 20% hydrochloric acid (100 g) and, after stirring at 80° C. for 3 hours, the mixture was allowed to stand and partitioned and then the mixture layer was cooled to 25° C. To this aqueous layer was added an aqueous 20% sodium hydroxide solution (101.7 g) to adjust the pH value to not less than 12, followed by extracting twice with toluene (100 g). Then, this organic layer was concentrated to obtain 6.58 g of nearly reacemized 1-(2,4-dichlorophenyl)ethlyamine as a colorless liquid. The yield thereof after correction of purity due to gas chromatography was 92.4%. The optical isomer ratio was as follows: S-form/R-form=52.2/47.8.

Example 2

(1) To a mixture of optically active 1-(2,4-dichlorophenyl) ethylamine (optical isomer ratio: S-form/R-form=62.5/37.5) (10 g), isobutylaldehyde (2-methylpropanol) (5.67 g) and toluene (100 g) was added p-toluenesulfonic acid (0.1 g), and then the mixture was heated under reflux while the formed water is removed from the system by using a water isolator for 5 hours.

The reaction mixture was cooled to 20° C. and washed with water (50 g). Toluene was distilled off from the organic layer after partitioning to obtain 12.3 g of optically active N-isobutylidene-α-(2,4-dichlorophenyl)ethylamine as a pale yellow oil. The yield thereof after correction of purity due to gas chromatography was 94.5%.

$^1$H-NMR (CDCl$_3$/TMS) δ value (ppm): 1.1 (2d, 6H), 1.4 (d, 3H), 2.5 (m, 1H), 4.7 (q, 1H), 7.1–7.7 (m, 4H)

(2) To this optically active N-isobutylidene-α-(2,4-dichlorophenyl)ethylamine (10 g) were added toluene (100 g) and N,N-dimethylformamide (10 g) and then sodium tert-butoxide (0.79 g), and the mixture was stirred at 80° C. for 8 hours. At this time, an aliquot of the reaction mixture was collected and the isomerization rate of N-isobutylidene-α-(2,4-dichlorophenyl)ethylamine was measured by gas chromatography. The ratio of N-(α-methyl-2,4-dichlorobenzylidene)-isobutylamine as the isomerized product was as follows: N-isobutylidene-α-(2,4-dichlorophenyl) ethylamine:N-(α-methyl-2,4-dichlorobenzylidene)-isobutylamine=97.8:2.2. This reaction mixture was cooled to 25° C. and poured into water (100 g), followed by stirring at 25° C. for 5 minutes. After the mixture was allowed to stand and partitioned, the aqueous layer was extracted with toluene (50 g) and then mixed with the organic layer obtained by the partition above.

(3) To this organic layer was added aqueous 20% hydrochloric acid (120 g) and, after stirring at 80° C. for 5 hours, the mixture was allowed to stand and partitioned and then the aqueous layer was cooled to 25° C. To this aqueous layer was added an aqueous 20% sodium hydroxide solution (120.7 g) to adjust the pH value to not less than 12, followed by extracting twice with toluene (100 g). Then, this organic layer was concentrated to obtain 7.31 g of nearly racemized 1-(2,4-dichlorophenyl)ethylamine as a colorless liquid. The yield thereof after correction of purity due to gas chromatography was 80.5%. The optical isomer ratio was as follows: S-form/R-form=55.3/44.7.

Example 3

According to the same manner as that described in Example 1 except for changing the optical isomer ratio of optically active 1-(2,4-dichlorophenyl)ethylamine to as follows: S-form/R-form=87/13) in Example 1 (1), using N-neopentylidene-α-(2,4-dichlorophenyl)ethylamine (6.7 g), toluene (41 g), dimethyl sulfoxide (6.7 g) and potassium tert-butoxide (0.58 g) in place of N-neopentylidene-α-(2,4-dichlorophenyl)ethylamine (10 g), toluene (100 g), N,N-dimethylformamide (10 g) and potassium tert-butoxide (0.74 g) and changing the reaction temperature to 30° C., the reaction was conducted to obtain 4.43 g of nearly racemized 1-(2,4-dichorophenyl)ethylamine. The yield thereof after correction of purity due to gas chromatography was 85.0%. The optical isomer ratio was as follows: S-form/R-form= 51.3/48.7. Aliquot of the reaction mixture was collected before hydrolysis and the isomerization rate was measured by gas chromatography. The results are as follows: N-neopentylidene-α-(2,4-dichlorophenyl)ethylamine:N-(α-methyl-2,4-dichlorobenzylidene)-neopentylamine=90.9:9.1

Reference Comparative Example 1

A mixture of optically active 1-(2,4-dichlorophenyl) ethylamine (optical isomer ratio: S-form/R-form=8/92) (5 g), dimethyl sulfoxide (50 g) and potassium tert-butoxide (1.21 g) was heated with stirring at 80° C. for 10 hours. After cooling to 25° C. or aliquot of the reaction solution was collected and the optical isomer ratio of 1-(2,4-dichlorophenyl)ethylamine was measured by a high performance liquid chromatography. As a result, a ratio of the S-form to the R-form was 8:92 and the racemization reaction did not proceed at all.

What is claimed is:

1. A process for racemization of an optically active 1-phenylethylamine derivative represented by the formula [1]:

wherein R$^1$ represents a phenyl group substituted at least at the ortho-position, which comprises reacting the optically active 1-phenylethylamine derivative [1] with an aldehyde compound represented by the formula [2]:

wherein R$^2$ represents an optionally substituted alkyl group or an optionally substituted phenyl group to form an optically active imine represented by the formula [3]:

wherein R$^1$ and R$^2$ are as defined above, reacting the imine with an alkaline metal tert-alkoxide in an aprotic polar solvent or a mixture of the aprotic polar solvent and an aprotic nonpolar solvent, and then hydrolyzing the resultant racemic imine.

2. The process according to claim 1, wherein the aprotic polar solvent is N,N-dimethylformamide or dimethyl sulfoxide and the aprotic nonpolar solvent is an aromatic hydrocarbon solvent.

3. The process according to claim 1 or 2, wherein the alkaline metal tert-alkoxide is sodium tert-butoxide or potassium tert-butoxide.

4. The process according to claim 1 or 2 wherein R$^1$ is a group represented by the general formula [4]:

wherein X represents a halogen atom or a lower alkyl group, and Y represents a halogen atom, a lower alkyl group or a hydrogen atom, and R$^2$ is a lower alkyl group.

5. The process according to claim 1 or 2, wherein R$^1$ is a 2,4-dichlorophenyl group and R$^2$ is a lower alkyl group.

* * * * *